United States Patent [19]
Beck et al.

[11] Patent Number: 6,036,980
[45] Date of Patent: *Mar. 14, 2000

[54] PROCESS FOR THE PRODUCTION OF GLUTAMIC ACID AND THE USE OF PROTEIN HYDROLYSATES IN THIS PROCESS

[75] Inventors: Roland Herwig Friedrich Beck, Everberg; Jos Willy Ghislain Corneel De Sadeleer, Holsbeek, both of Belgium; Jacobus Stephanus Vercouteren, Sas van Gent, Netherlands

[73] Assignee: Cerestar Holding B.V., Van Gent, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/938,815

[22] Filed: Sep. 26, 1997

[30] Foreign Application Priority Data

Sep. 27, 1996 [GB] United Kingdom .................. 9620144

[51] Int. Cl.⁷ ....................................... A23B 7/10
[52] U.S. Cl. ................. 426/49; 426/52; 426/650
[58] Field of Search ................. 426/49, 52, 18, 426/48, 534, 650, 656

[56] References Cited

U.S. PATENT DOCUMENTS

| | | |
|---|---|---|
| 3,042,585 | 7/1962 | Ogawa . |
| 3,212,994 | 10/1965 | Kono . |
| 3,852,479 | 12/1974 | Yokotsuka . |

FOREIGN PATENT DOCUMENTS

| | | |
|---|---|---|
| 578 572 | 1/1994 | European Pat. Off. . |
| 788335 | 12/1957 | United Kingdom . |
| 964623 | 7/1964 | United Kingdom . |
| 981358 | 1/1965 | United Kingdom . |
| 993699 | 6/1965 | United Kingdom . |
| 1096882 | 12/1967 | United Kingdom . |
| 1118827 | 7/1968 | United Kingdom . |
| 95/28853 | 11/1995 | WIPO . |

OTHER PUBLICATIONS

Database WPI, Section CH, Week 9438 Derwent Publication Ltd., London,GB; Class B05,AN 94–309059 XP002029450 & RO 107 002 B (Caraiani t), Aug. 30, 1993.

Database WPI, Section Ch, Week 7527 Derwent Publication Ltd., London GB; Class D13,AN 75–45161W XP002029451, JP 50 019 995 A (Kikkoman Shoyu CO LTD.) Mar. 3, 1975.

Database WPI Section Ch, Week 7551 Derwent Publication Ltd., London,GB; Class B05, AN 75–84005W XP002029452 & JP 50 111 284 A (Ajinomoto KK), 1.

*Primary Examiner*—Leslie Wong
*Attorney, Agent, or Firm*—Pillsbury Madison & Sutro LLP

[57] ABSTRACT

The present process concerns the production of glutamic acid or glutamate. The process of the present invention includes the following steps. Glutamine or glutamic acid rich proteins are hydrolysed. Optionally, the glutamic acid is converted to glutamate and the glutamate is isolated. The protein hydrolysate or the glutamate depleted protein hydrolysate is added to the feedstock of a glutamic acid fermentation in such an amount that the protein hydrolysate forms the major carbon and nitrogen source. After fermentation the glutamic acid is converted to glutamate and the glutamate is isolated.

10 Claims, 1 Drawing Sheet

PROCESS FOR THE PRODUCTION OF GLUTAMIC ACID AND THE USE OF PROTEIN HYDROLYSATES IN THIS PROCESS

TECHNICAL FIELD

The present invention relates to a process for the fermentative production of glutamic acid/glutamate. The invention specifically relates to the use of protein hydrolysates as a fermentation feedstock in this process wherein the protein hydrolysate is present as the major assimilable carbon and nitrogen source. Furthermore, the invention relates to the glutamic acid or glutamate obtained using the presented process.

BACKGROUND OF THE INVENTION

There is an increasing demand for the amino acid, glutamic acid in the form of its sodium salt; monosodium glutamate (MSG). This demand is due to the use of MSG as a flavour enhancer in food applications in amongst others meat, sauces and soya-based products.

L-glutamic acid is made commercially by fermentation especially in Japan and in the USA. Microbial strains belonging to the species *Micrococcus glutamicus, Brevibacterium divaricatum, Brevibacterium aminogenes, Brevibacterium flavum, Bacillus megaterium* and *Microbacterium salicinovorum* but also species belonging to the genus Corynebacterium amongst others have been used to obtain glutamic acid by fermentation. Yields of more than 40 g/100 g sugar supplied have been reported.

British patent GB 993,699 relates to a process for producing L-glutamic acid using a novel strain of *Microbacterium ammoniaphilum* it is mentioned that a wheat protein hydrolysate can be used as an amino acid source that is as a growth nutrient, urea being used as the nitrogen source. Before such a hydrolysate is used the L-glutamic acid is first removed. Ordinary carbohydrates are used as the carbon source.

Other strains which are used for the production of L-glutamic acid are disclosed in the following patents GB 964,623 (*Brevibacterium divaricatum* sp strain), GB 788,335 Cephalosporium species) and U.S. Pat. No. 3,042,585 (*Bacillus circulans*).

Patents GB 981,358, GB 1,096,882, GB 1,118,827 and U.S. Pat. No. 3,212,994 disclose the use of strains which are capable of growing on less costly carbon sources including different types of molasses.

European patent application EP 578 572 discloses a process for preparing a protein hydrolysate which is rich in glutamate. The process comprises the steps of enzymatic hydrolysis of proteinaceous material followed a by a treatment with bakers yeast. After autolysis of the yeast glutaminase is liberated which converts the glutamic acid to glutamate.

A different process for obtaining glutamic acid is via the hydrolysis of glutamine/glutamic acid rich proteins. The isolated glutamine-rich protein is hydrolysed using acid- and/or enzyme-conversion under the appropriate pH and temperature conditions. The product is further treated if necessary. Finally, the glutamic acid is obtained which may be further converted to glutamate. The drawback of this later method is that the other amino acids which are released during hydrolysis require the product to be extensively purified (three times crystallised) and furthermore that the other amino acids are lost as nitrogen containing waste.

Other patents relating to protein hydrolysate preparations and to sauces containing these hydrolysates are U.S. Pat. No. 3,852,479 and WO 95/28853.

It would therefore be useful to have a process starting from protein hydrolysates wherein the amino acids which would otherwise be lost are converted to glutamic acid/glutamate and which would also give rise to less extensive purification. The present invention provides such a process.

SUMMARY OF THE INVENTION

The present invention discloses a process for obtaining glutamic acid characterised in that a glutamine/glutamic acid rich protein is hydrolysed and the hydrolysate is used as the major carbon and nitrogen source of a fermentation feedstock for the production of glutamic acid. The protein hydrolysate contains a substantial amount of glutamic acid which may be isolated before the use of the hydrolysate as a feedstock. The protein hydrolysate either before or after the isolation of the glutamic acid is used to prepare glutamic acid by fermentation.

The glutamic acid isolated before and after the fermentation is then further purified and converted to glutamate by neutralisation or ion-exchange.

The invention also discloses the use of a glutamic acid/glutamine rich protein hydrolysate as a fermentation feedstock.

DETAILED DESCRIPTION OF THE INVENTION

Figure 1:
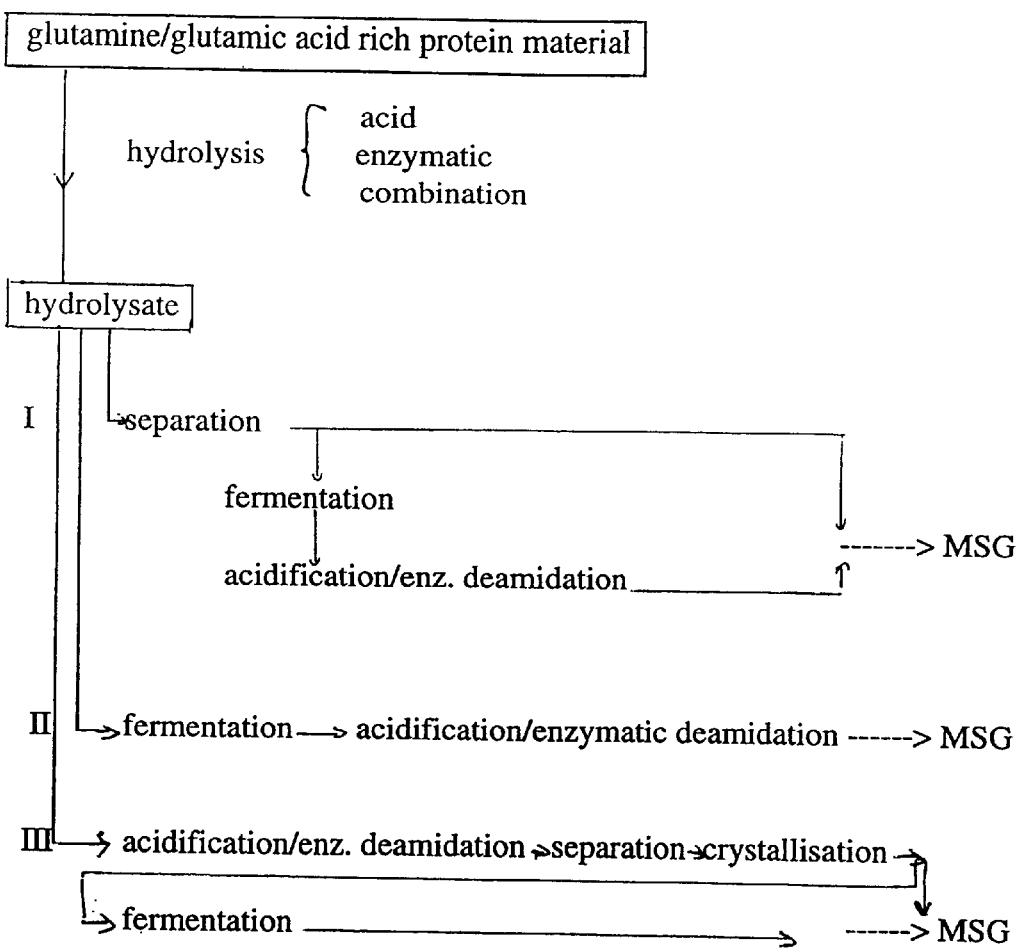
FIG. 1 describes the alternative pathways for performing the process of the present invention.

The overall process of the present invention is schematically represented in FIG. 1. The present invention discloses a process for obtaining glutamic acid characterised in that a) a glutamine/glutamic acid rich protein is hydrolysed to obtain a protein hydrolysate, b) the protein hydrolysate is used as the major carbon and nitrogen source of a fermentation feedstock for glutamic acid fermentation, c) a glutamic acid fermentation is performed.

The present invention also discloses a process for obtaining glutamate characterised in that the glutamic acid obtained from the fermentation of a glutamine/glutamic acid rich protein hydrolysate is converted to glutamate. This conversion can be achieved by simple neutralisation for example by ion-exchange.

It is also possible to isolate the glutamic acid from the protein hydrolysate before performing the fermentation.

The glutamine/glutamic acid rich proteins used as a starting material for the present process are obtained from grains of the family Gramineae preferred tribes are grains from the Andropogoneae, the Hordeae and the Maydeae from which tribes the preferred grains are sorghum, wheat and corn, respectively. The proteins are for example gluten, these may be cereal gluten or gluten from corn or sorghum, preferably wheat or corn gluten are used. Gluten are commercially available in an impure dried form containing 75–80% protein, the non-protein part is mainly 5–15% carbohydrates, consisting of residual starch. The remaining 5–15% consists mainly of a mixture of lipids. The gluten are also available in wet form.

The glutamine/glutamic acid rich proteins are dispersed in water and kept at certain temperature and pH values. The proteins are hydrolysed through the addition of acid and/or enzymes and the hydrolysation is allowed to proceed for the desired amount of time. It is known that during subsequent fermentation some of the microorganisms which are employed produce proteases. If this is the case it is possible to stop the hydrolysis at a stage where only a part of the proteins have been hydrolysed. The glutamine/glutamic acid rich proteins are for example gluten. Depending on the source the gluten contain up to 40% glutamic acid or glutamine.

Typical hydrolysis conditions are pH 3–11, optimum yields of L-glutamic acid have been reported using 30% acid solution, for 5 hours at 113 degrees. Alkaline hydrolysis has also been described although care has to be taken that this results in some loss of L-glutamic acid due to racemisation. When enzymes are used different types of proteases are used under conditions depending on the type and source of the enzyme. A combination of acid- and enzymatic hydrolysis is also possible.

The hydrolysate is used as an ingredient notably as a carbon- and nitrogen source in a fermentation medium i.e. as a feedstock. It is possible to use the complete hydrolysate as a fermentation feedstock. To improve the quality of the fermentation broth it may be necessary to remove the insoluble particles by mechanical separation, filtration, decantation etc. Alternatively, it is possible to isolate the glutamic acid from the hydrolysate before fermentation.

Although in principle different amino acids can be made from the gluten hydrolysate, we have found that it is particularly interesting to make glutamic acid. Prior to the fermentation it may be useful to separate (a part of) the glutamic acid from the rest of the hydrolysate. It is preferable in such a case to acidify the hydrolysate or to enzymatically deamidate the product so that the glutamic acid or glutamate can be isolated. The glutamate can be obtained by direct crystallisation or by chromo-separation followed by crystallisation. The resulting hydrolysate is then used as fermentation feedstock. This results in a further conversion of amino acid and peptide material to the desired glutamic acid/glutamate resulting in an increased overall yield and a waste stream containing apart from the biomass less ingredients.

Amino acid fermentations and notably the fermentation to obtain glutamic acid are well-known and have been extensively reviewed see for example 'Amino acids' by K. Nakayama Chapter 17 pp748–801 in Prescott & Dunn's Industrial Microbiology Ed. G. Reed, 4th ed. 1982. Microorganisms capable of producing glutamic acid are widely available strains from the following genera are used Micrococcus, Brevibacterium, Microbacterium, Corynebacterium, Bacillus and Cephalosporium, more preferably strains from the genera Corynebacterium, Brevibacterium and Microbacterium.

The protein hydrolysate is used to replace the ammonia which would otherwise be required in the fermentation feedstock. A relatively small amount of amino acid would be enough to meet the nitrogen requirement. The protein hydrolysate is used to partially or completely replace the carbon source (normally glucose or other carbohydrates) in addition to the nitrogen source. Other carbon and nitrogen sources and further growth increasing ingredients are added if needed as long as the protein hydrolysate remains the major carbon and nitrogen source.

The present invention also discloses the use of a glutamic acid-rich protein hydrolysate as a fermentation feedstock for the preparation of glutamic acid which may subsequently be converted to glutamate. Until the present invention was made the hydrolysates were not used as fermentation feedstock replacing the major part of both the carbon and the nitrogen source.

EXAMPLE 1

Commercially available wheat gluten is dispersed in at 30% d.s. in a 1 N HCl solution. Hydrolysis is continued for 24 hours. The hydrolysate is brought on an ion-exchange column and the product is eluted using a 0.2 N sodium citrate solution at pH 3.25. The glutamic acid is caught separately and the amount is determined.

The other amino acid fractions are pooled and added to a fermentation medium.

The protein hydrolysate is used as a nitrogen and carbon source and thereby replaces ammonia and glucose.

The microorganism selected for the fermentation is selected from strains of the genera Micrococcus, Brevibacterium, Microbacterium, Corynebacterium, Bacillus and Cephalosporium.

After a fermentation time of between 1 and 4 days the biomass is separated from the fermentation medium, the medium is then passed over an ion-exchange column. The amounts of the amino acids are determined. It is found that the total amount of glutamic acid after hydrolysis and fermentation is higher than after hydrolysis alone. It is further found that the cumulative amounts of the other amino acids is lower after fermentation than before.

Finally, the glutamic acid is converted to sodium glutamate by neutralisation or ion-exchange.

EXAMPLE 2

Gluten are hydrolysed as described in Example 1. The amount of glutamic acid is determined through amino acid analysis of a sample of the hydrolysate. The insoluble particles are removed from the hydrolysate by filtration. The complete hydrolysate is used as a fermentation feedstock. After fermentation the amount of glutamic acid is found to be higher than before fermentation. The glutamic acid is converted to glutamate.

What is claimed is:

1. A process for obtaining glutamic acid comprising:
   a) hydrolyzing a gluten as a glutamine/glutamic acid rich protein to obtain a protein hydrolysate,
   b) using the protein hydrolysate as the sole carbon and nitrogen source of a fermentation feedstock for glutamic acid fermentation, and
   c) effecting a glutamic acid fermentation using said fermentation feedstock.

2. A process for obtaining a glutamate consisting essentially of:
   a) hydrolyzing a gluten as a glutamine/glutamic acid rich protein to obtain a protein hydrolysate,
   b) using the protein hydrolysate as the sole carbon and nitrogen source of a fermentation feedstock for glutamic acid fermentation, and
   c) effecting a glutamic acid fermentation using said fermentation feedstock.
   d) converting glutamic acid obtained from said glutamic acid fermentation to a glutamate via neutralization.

3. A process according to claim 1, wherein said process further comprises:
   first treating said protein hydrolysate to convert glutamic acid to glutamate and then at least partially removing glutamic acid or glutamate from the hydrolysate before using the hydrolysate as a fermentation feedstock.

4. A process according to claim 1, wherein said gluten is obtained from wheat, corn or sorghum.

5. A process according to claim 1, wherein said fermentation is effected with the use of a microorganism selected from the group consisting of Micrococcus, Brevibacterium, Microbacterium, Corynebacterium, Bacillus and Cephalosporium.

6. A process according to claim 5, wherein said microorganism is selected from group consisting of Corynebacterium, Brevibacterium or Microbacterium.

7. A process according to claim 1 or 2, wherein said hydrolyzing is effected through the addition of acid.

8. A process according to claim 5, wherein said microorganism is selected from the group consisting of Micrococcus, Brevibacterium, Coryrebacterium, Bacillus and Cephalosporium.

9. A process for preparing glutamic acid comprising:
(a) hydrolyzing gluten to obtain a protein rich hydrolysate, containing glutamic acid;
(b) recovering solids from said protein hydrolysate and, optionally, recovering the glutamic acid from said protein rich hydrolysate to obtain a resulting hydrolysate;
(c) providing, as feedstock, an ammonia and glucose-free nitrogen and carbon source consisting essentially of said resulting hydrolysate;
(d) effecting a glutamic acid fermentation using said resulting hydrolysate to obtain glutamic acid.

10. A process for preparing glutamic acid consisting essentially of fermenting a feedstock which is glucose free, said feedstock consisting of a gluten protein hydrolysate, under effective fermentation conditions, accumulating glutamic acid, and recovering said glutamic acid.

* * * * *